(12) United States Patent
Hoeffkes et al.

(10) Patent No.: US 6,537,330 B1
(45) Date of Patent: Mar. 25, 2003

(54) COLORANTS

(75) Inventors: Horst Hoeffkes, Duesseldorf (DE);
Klaus Schumann, Erkrath (DE);
Winifried Neuhaus, Mettmann (DE)

(73) Assignee: Henkel Kommanditgesellschaft auf Aktien, Duesseldorf (DE)

(*) Notice: Subject to any disclaimer, the term of this patent is extended or adjusted under 35 U.S.C. 154(b) by 0 days.

(21) Appl. No.: 09/338,101

(22) Filed: Jun. 23, 1999

Related U.S. Application Data

(60) Provisional application No. 60/093,926, filed on Jul. 23, 1998.

(30) Foreign Application Priority Data

Jun. 23, 1998 (DE) ......................................... 198 27 000

(51) Int. Cl.$^7$ ................................................. A61K 7/13
(52) U.S. Cl. ....................... 8/409; 8/405; 8/406; 8/407; 8/408; 8/423
(58) Field of Search ............................ 8/405, 406, 407, 8/408, 409, 423

(56) References Cited

U.S. PATENT DOCUMENTS

| | | | |
|---|---|---|---|
| 2,934,396 A | 4/1960 | Charle et al. ................... | 8/423 |
| 3,194,734 A | 7/1965 | Seemuller et al. ............. | 8/423 |
| 3,649,160 A | 3/1972 | Kalopissis et al. ............. | 8/409 |
| 3,861,868 A | 1/1975 | Milbrada | |
| 3,993,436 A * | 11/1976 | Fujinuma ....................... | 8/406 |
| 4,013,404 A | 3/1977 | Parent et al. ................... | 8/423 |
| 4,200,432 A | 4/1980 | Kalopissis et al. | |
| 4,425,132 A * | 1/1984 | Grollier et al. ................. | 8/405 |
| 4,595,765 A | 6/1986 | Murphy ....................... | 548/491 |
| 4,750,908 A | 6/1988 | Rosenbaum et al. | |
| 4,797,130 A | 1/1989 | Clausen et al. | |
| 4,808,190 A | 2/1989 | Grollier et al. | |
| 4,822,375 A | 4/1989 | Lang et al. | |
| 4,865,774 A | 9/1989 | Fabry et al. ................. | 252/554 |

(List continued on next page.)

FOREIGN PATENT DOCUMENTS

| | | | |
|---|---|---|---|
| CA | 2222363 | * | 6/1998 |
| DE | 22 15 303 | | 10/1972 |
| DE | 1 916 139 | | 8/1977 |
| DE | 37 23 354 | | 1/1989 |
| DE | 37 25 030 | | 2/1989 |
| DE | 39 26 344 | | 8/1989 |
| DE | 43 35 623 | | 4/1995 |
| DE | 43 35 626 | | 4/1995 |
| DE | 4335626 | * | 4/1995 |
| DE | 44 09 143 | | 9/1995 |
| DE | 197 32 975 | | 7/1997 |
| DE | 19637966 | * | 2/1998 |
| DE | 197 17 282 | | 10/1998 |
| EP | 0 337 853 | | 5/1992 |
| EP | 0 530 229 | | 6/1995 |
| EP | 0 740 931 | | 11/1996 |
| EP | 0 462 857 | | 3/1998 |
| FR | 2 008 797 | | 1/1970 |
| GB | 2 033 392 | | 5/1980 |
| GB | 2 211 517 | | 7/1989 |
| GB | 2 213 169 | | 8/1989 |
| JP | 01 233 210 | | 9/1989 |
| WO | WO91/17739 | | 11/1991 |
| WO | WO94/08970 | | 4/1994 |
| WO | 95/09629 | * | 4/1995 |
| WO | WO95/20103 | | 7/1995 |
| WO | 98/47473 | * | 10/1998 |
| WO | 99/15139 | * | 4/1999 |

OTHER PUBLICATIONS

CA record of Lysine, N6–lauroyl–; L–(6CI), Mar. 20, 2002.*
CA record of isatin, Mar.21, 2002.*
Derwent Abstracts 1995–156248 [21] (1995) for DE43 35 623 A1, Apr. 1995.
Journal of Chemical Society (C), Vol. 15, 1979, (Newcastle upon Tyne, GB), F. Binns, et al.: Studies Related to the Chemistry of Melanins. Part XIII. Sutdies on the Structures of Dopamine Melanen, pp. 2063–2070.
Journal of Chemical Society (C), 1967, (Newcastle upon Tyne), S.N. Mishra, et al.: Studies Related to the chemistry of Melanins. Part III. Systhesis of 5,6–Diydroxyindoline, pp. 1424–1427.
Journal of Medicinal Chemistry, vol. 21, No. 6, 1978, (University of California, San Francisco, California), C.G. Chavdarian, et al.: Oxidative And Cardioascular Studies On Natural And Synthetic Catecholaamines, pp. 548–554.
Kirk–Othmer Encyclopedia of Chemical Tehnology, vol. 12, 3rd Ed. John Wiley & Sons, NY, p. 101 No date available.
EU Inventory of Cosmetic Ingredients, Colipa, Mar. 1996— on diskette.
Derwent Abstract No. 70–23899R/15, of DE 1961139, Aug. 1977.
The Science of Hair Care, Chapter 7, pp. 235–261 and Chapter 8, pp. 263–286 (1986).
Derwent Patent Abstract (WPAT) No. 89–033330/05, of DE 3725030, Feb. 1989.
Derwent Patent Abstract (WPAT) No. 89–016906/03, of DE 3723354, Jan. 1989.
Derwent Patent Abstract (WPAT) No. 91–073475/10, of DE 3926344, Feb. 1991.
Derwent Patent Abstract (WPAT) No. 96–487191/49, of EP 740931, Nov. 1996.

Primary Examiner—Margaret Einsmann
(74) Attorney, Agent, or Firm—Stephen D. Harper; Glenn E. J. Murphy; Gregory M. Hill

(57) ABSTRACT

A composition for coloring keratin fibers, containing an indoline, an indole, or a derivative thereof in combination with at least one amino acid or oligopeptide. The composition is useful for coloring human hair and restoring grey hair to its natural color. The formulation can be applied with atmospheric oxygen as the sole oxidizing agent.

17 Claims, No Drawings

U.S. PATENT DOCUMENTS

| | | | | |
|---|---|---|---|---|
| 4,886,549 | A | 12/1989 | Koci | |
| 4,888,027 | A | 12/1989 | Grollier et al. | |
| 4,921,503 | A | 5/1990 | Anderson et al. | |
| 4,923,479 | A | 5/1990 | Braun | |
| 4,931,218 | A | 6/1990 | Schenker et al. | 252/551 |
| 4,985,955 | A | 1/1991 | Grollier et al. | |
| 5,011,500 | A | 4/1991 | Grollier et al. | 8/410 |
| 5,021,067 | A | 6/1991 | Grollier | 8/409 |
| 5,034,015 | A | 7/1991 | Junino et al. | |
| 5,073,174 | A | 12/1991 | Vayssie et al. | |
| 5,096,455 | A | 3/1992 | Grollier | |
| 5,104,413 | A | 4/1992 | Ikeda | |
| 5,131,911 | A | 7/1992 | Lang et al. | |
| 5,131,912 | A | 7/1992 | Ehara et al. | |
| 5,135,544 | A | 8/1992 | Grollier et al. | |
| 5,167,669 | A | 12/1992 | Grollier | |
| 5,178,637 | A | 1/1993 | Lagrange et al. | 8/405 |
| 5,180,396 | A | 1/1993 | Grollier et al. | |
| 5,190,564 | A | 3/1993 | Lang et al. | |
| 5,207,798 | A | 5/1993 | Cotteret et al. | |
| 5,254,135 | A | 10/1993 | Lang et al. | |
| 5,261,926 | A | 11/1993 | Lang et al. | |
| 5,279,616 | A | 1/1994 | Lang et al. | |
| 5,279,617 | A | 1/1994 | Prota et al. | |
| 5,279,618 | A | 1/1994 | Prota et al. | |
| 5,279,620 | A | 1/1994 | Junino et al. | |
| 5,294,726 | A | 3/1994 | Behler et al. | 554/98 |
| 5,340,366 | A | 8/1994 | Lang et al. | |
| 5,364,414 | A | 11/1994 | Lang et al. | |
| 5,368,610 | A | 11/1994 | Chan et al. | |
| 5,391,206 | A | 2/1995 | Cotteret | |
| 5,399,713 | A | 3/1995 | Knuebel et al. | 548/490 |
| 5,413,612 | A | 5/1995 | Wenke | 8/423 |
| 5,421,833 | A | 6/1995 | Lorenz | |
| 5,425,993 | A | 6/1995 | Morancais et al. | 428/402.24 |
| 5,427,588 | A | 6/1995 | Lagrange et al. | |
| 5,441,542 | A | 8/1995 | Prota et al. | |
| 5,478,360 | A | 12/1995 | Grollier et al. | |
| 5,492,541 | A | 2/1996 | Murphy et al. | |
| 5,494,490 | A | 2/1996 | Audousset et al. | |
| 5,496,543 | A * | 3/1996 | Lagrange et al. | |
| 5,516,916 | A | 5/1996 | Murphy et al. | |
| 5,518,505 | A | 5/1996 | Cotteret | |
| 5,538,517 | A | 7/1996 | Samain et al. | 8/423 |
| 5,540,738 | A | 7/1996 | Chan et al. | |
| 5,556,989 | A | 9/1996 | Lagrange et al. | |
| 5,578,087 | A | 11/1996 | Audousset et al. | |
| 5,583,234 | A | 12/1996 | Lagrange et al. | 548/455 |
| 5,584,889 | A | 12/1996 | Wenke et al. | |
| 5,609,649 | A | 3/1997 | Junino et al. | |
| 5,609,650 | A | 3/1997 | Knuebel et al. | 8/423 |
| 5,611,817 | A * | 3/1997 | Moeller et al. | 8/405 |
| 5,620,484 | A | 4/1997 | Maubru | 8/409 |
| 5,628,799 | A | 5/1997 | Wenke et al. | |
| 5,670,099 | A | 9/1997 | Morancais et al. | 8/647 |
| 5,683,474 | A | 11/1997 | Cotteret et al. | |
| 5,690,697 | A | 11/1997 | Samain | 8/423 |
| 5,704,948 | A | 1/1998 | Terranova et al. | 8/409 |
| 5,704,949 | A | 1/1998 | Prota et al. | 8/423 |
| 5,735,909 | A | 4/1998 | Maubru | 8/412 |
| 5,743,919 | A | 4/1998 | Moeller et al. | 8/409 |
| 5,752,982 | A | 5/1998 | Lang et al. | 8/409 |
| 5,752,983 | A | 5/1998 | Audousset et al. | 8/409 |
| 5,753,214 | A | 5/1998 | Yoshioka et al. | |
| 5,755,829 | A | 5/1998 | Terranova et al. | 8/409 |
| 5,766,576 | A | 6/1998 | Löwe et al. | |
| 5,769,902 | A | 6/1998 | Samain | 8/409 |
| 5,769,903 | A | 6/1998 | Audousset et al. | 8/409 |
| 5,776,497 | A | 7/1998 | Lagrange et al. | 424/489 |
| 5,785,717 | A | 7/1998 | Maubru et al. | 8/409 |
| 5,792,220 | A | 8/1998 | Wenke et al. | 8/409 |
| 5,795,354 | A | 8/1998 | Rippon | 8/405 |
| 5,814,106 | A | 9/1998 | Audousset | 8/409 |
| 5,827,330 | A | 10/1998 | Wenke et al. | 8/423 |
| 5,851,237 | A | 12/1998 | Anderson et al. | |
| 5,858,024 | A | 1/1999 | De Lacharriere et al. | 8/408 |
| 5,868,800 | A | 2/1999 | Cotteret et al. | 8/410 |
| 5,876,465 | A | 3/1999 | Terranova et al. | 8/409 |
| 5,938,792 | A | 8/1999 | Lang et al. | 8/409 |
| 5,948,121 | A | 9/1999 | Aaslyng et al. | |
| 5,954,871 | A | 9/1999 | Nicolas-Morgantini et al. | 8/127.5 |
| 5,961,667 | A * | 10/1999 | Doehling et al. | 8/408 |
| 5,968,206 | A | 10/1999 | Audousset et al. | 8/409 |
| 5,976,195 | A | 11/1999 | de la Mettrie et al. | |
| 5,980,586 | A | 11/1999 | Wenke et al. | |
| 6,001,135 | A | 12/1999 | Rondeau et al. | 8/407 |
| 6,002,018 | A | 12/1999 | Terranova et al. | 548/484 |
| 6,004,356 | A | 12/1999 | Audousset | 8/412 |
| 6,010,541 | A | 1/2000 | de la Mettrie et al. | 8/412 |
| 6,036,729 | A | 3/2000 | Barfoed et al. | |
| 6,042,620 | A | 3/2000 | Braun et al. | |
| 6,063,136 | A | 5/2000 | Vidal et al. | |
| 6,074,438 | A | 6/2000 | Lim et al. | |
| 6,074,439 | A | 6/2000 | De La Mettrie et al. | |
| 6,077,320 | A * | 6/2000 | Andrean et al. | |
| 6,090,159 | A | 7/2000 | Maubru | |
| 6,090,160 | A | 7/2000 | Junino et al. | |
| 6,090,161 | A | 7/2000 | Hoeffkes et al. | |
| 6,093,219 | A | 7/2000 | Audousset et al. | |
| 6,099,590 | A | 8/2000 | Maubru | |
| 6,099,592 | A | 8/2000 | Vidal et al. | |
| 6,099,593 | A | 8/2000 | Terranova et al. | |
| 6,106,577 | A | 8/2000 | Audousset et al. | |
| 6,129,770 | A | 10/2000 | Deutz et al. | |
| 6,132,475 | A | 10/2000 | Chassot et al. | |
| 6,143,286 | A | 11/2000 | Bhambhani et al. | |
| 6,146,429 | A * | 11/2000 | Gast et al. | |
| 6,152,967 | A | 11/2000 | Maubru | |
| 6,156,076 | A | 12/2000 | Casperson et al. | |
| 6,165,230 | A | 12/2000 | Rose et al. | |
| 6,171,347 | B1 | 1/2001 | Kunz et al. | |

* cited by examiner

COLORANTS

This application claims benefit of U.S. Provisional Application Ser. No. 60/093,926 filed Jul. 23, 1998.

BACKGROUND OF THE INVENTION

This invention relates to formulations for coloring keratin fibers, more particularly human hair, which contain special dye precursors of the indole or indoline type and a component for intensifying and/or shading the color, to the use of this component for intensifying and/or shading colors and to corresponding coloring processes.

Among the various products available for the cosmetic treatment of the human body, formulations for modifying or shading the color of the hair occupy a prominent position. Disregarding blonding preparations which lighten the hair oxidatively by degrading the natural hair dyes, two types of colorants have long been of importance in the coloring of hair:

So-called oxidation colorants are used for permanent, intensive colors with corresponding fastness properties. Oxidation colorants normally contain oxidation dye precursors, so-called primary intermediates and secondary intermediates. The primary intermediates form the actual dyes with one another or by coupling with one or more secondary intermediates under the influence of oxidizing agents or atmospheric oxygen. Although oxidation colorants are distinguished by excellent coloring results, they can also be attended by disadvantages for certain narrow circles of people. Thus, certain dye precursors can cause unwanted skin irritation in so-called "para-allergics". In addition, oxidation dyes are generally developed with oxidizing agents, more particularly hydrogen peroxide. In the event of frequent application by people with sensitive hair, this can cause harm or even damage to the hair structure which has to be repaired with special hair-care products. It is also important not to underestimate the number of people who, in the context of the popular "natural-versus-chemical" debate, avoid using chemical products wherever possible because of their personal feelings.

Colorants or tints containing substantive dyes as their coloring component are normally used for temporary colors. Substantive dyes are based on dye molecules which are directly absorbed onto the hair and do not require an oxidative process for developing the color. Dyes such as these include, for example, henna which has been used since ancient times for coloring the body and hair.

However, since in the eyes of many consumers both coloring processes are tainted by a hint of the "artificial" with its negative associations, a new coloring process has recently attracted considerable attention. In this process, precursors of the natural hair dye melanin are applied to the hair and, through oxidative processes in the hair, form near-natural dyes. A corresponding process using 5,6-dihydroxyindoline as dye precursor is described in EP-B1 530 229. By application and, more particularly, frequent application of formulations containing 5,6-dihydroxyindoline, grey hair can be restored to its natural color. The color can be developed with atmospheric oxygen as sole oxidizing agent so that there is no need to use other oxidizing agents.

Under the described conditions, however, satisfactory results can only be achieved in people who, before "going grey", had medium blond to dark brown hair. Accordingly, there has been no shortage of attempts to modify this known coloring process in such a way that even originally red and, above all, dark to black hair can be restored to its original color.

One method of obtaining dark to black color tones, particularly those described by experts as "flat", is the subject of German patent application 197 32 975.6 to which reference is expressly made, particularly in regard to the prior art literature cited therein. The solution proposed in this patent application is to add conventional secondary intermediates. Although the color can be developed with atmospheric oxygen alone, the use of at least one other oxidizing agent is recommended as a preferred alternative.

However, in view of the above-mentioned reservations of many consumers, there is still a need for a formulation which restores grey hair to its natural color, even in people with originally dark to black hair, without any need for purely synthetic dye components or to use other oxidizing agents than atmospheric oxygen.

It has now surprisingly been found that the problem stated above can be solved by application of a formulation which, besides known dye precursors of the indole or indoline type, contains at least one amino acid or oligopeptide.

DESCRIPTION OF THE INVENTION

Accordingly, the present invention relates to formulations for coloring keratin fibers, more particularly human hair, containing a dye precursor selected from the group consisting of indoline derivatives and indole derivatives, characterized in that it additionally contains at least one amino acid or oligopeptide.

Amino acids in the context of the invention are substances which contain at least one amino group and at least one —COOH or —$SO_3H$ group.

Preferred amino acids are aminocarboxylic acids, more particularly α-aminocarboxylic acids and ω-aminocarboxylic acids. Among the α-aminocarboxylic acids, arginine, lysine, ornithine and histidine are particularly preferred.

The amino acids are preferably added to the formulations according to the invention in free form. However, the amino acids may also be used in salt form. Preferred salts are the compounds containing hydrohalic acids, more particularly hydrochlorides and hydrobromides.

A particularly preferred amino acid is arginine used in particular in free form but also as the hydrochloride.

The present invention does of course also encompass formulations containing two or more amino acids or oligopeptides. In this case, combinations of arginine with another amino acid or oligopeptide are preferred.

In addition, the amino acids may also be used in the form of oligopeptides and protein hydrolyzates providing steps are taken to ensure that the necessary quantities of compounds conforming to the definition of amino acids according to the invention are present. Reference is expressly made in this connection to the disclosure of DE-OS 22 15 303.

The formulations according to the invention contain the amino acid or oligopeptide in quantities of preferably 0.1 to 10% by weight and more preferably 1 to 4% by weight, based on the formulation as a whole.

Hair colorants, more particularly those where the color is developed oxidatively with atmospheric oxygen or other oxidizing agents, such as hydrogen peroxide, are normally adjusted to a mildly acidic or alkaline pH value, i.e. to a pH value in the range from about 5 to 11. To this end, the colorants contain alkalizing agents, normally alkali metal or alkaline earth metal hydroxides, ammonia or organic amines.

In one special embodiment of the present invention, the amino acid or the oligopeptide is used not only to promote color development, but also at least partly as an alkalizing agent. Accordingly, amino acids and oligopeptides of which 2.5% by weight solutions in water have a pH value of 9 or higher are preferably used in this embodiment. One such amino acid is the preferred arginine. In this particular embodiment, the other alkalizing agent is selected from the group consisting of monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine and alkali metal and alkaline earth metal hydroxides. Within this group, monoethanolamine, triethanolamine and 2-amino-2-methylpropanol and 2-amino-2-methyl-1,3-propanediol are particularly preferred. ω-Amino acids, such as ω-aminocaproic acid, are also preferably used as alkalizing agents in this embodiment of the invention.

Particularly advantageous properties are exhibited by formulations in which the amino acid or the oligopeptide and the other alkalizing agent are present in a ratio by weight of 1:5 to 5:1. Quantity ratios of 1:2 to 2:1 have proved to be particularly suitable.

The formulations according to the invention contain a dye precursor of the indole or indoline type as another compulsory component.

According to the invention, preferred indoles and indolines are those which contain at least one hydroxy or amino group, preferably as a substituent on the six-membered ring. These groups may carry other substituents, for example in the form of etherification or esterification of the hydroxy group or alkylation of the amino group. Compounds containing two of these groups, particularly two hydroxy groups, of which one or both may be etherified or esterified are particularly preferred.

According to the invention, particularly preferred dye precursors are derivatives of indoline, such as 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 4-, 6- and 7-hydroxyindoline, 6-aminoindoline and 4-amino-indoline.

Most particularly preferred dye precursors are derivatives of 5,6-dihydroxyindoline corresponding to formula (Ia):

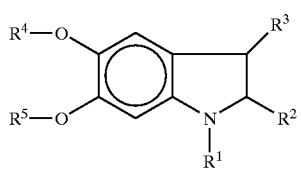

(Ia)

in which—independently of one another
R$^1$ is hydrogen, a C$_{1-4}$ alkyl group or a C$_{1-4}$ hydroxyalkyl group,
R$^2$ is hydrogen or a —COOH group which may even be present as a salt
with a physiologically compatible anion,
R$^3$ is hydrogen or a C$_{1-4}$ alkyl group,
R$^4$ is hydrogen, a C$_{1-4}$ alkyl group or a group —CO—R$^6$ where R$^6$ is a C$_{1-4}$ alkyl group,
R$^5$ stands for one of the groups mentioned for R$^4$,
or a physiologically compatible salt of these compounds with an organic or inorganic acid.

According to the invention, preferred representatives are 5,6-dihydroxyindoline, N-methyl-5,6-dihydroxyindoline, N-ethyl-5,6-dihydroxy-indoline, N-propyl-5,6-dihydroxyindoline, N-butyl-5,6-dihydroxyindoline. The parent compound, 5,6-dihydroxyindoline, is most particularly preferred.

According to the invention, preferred indoles are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole, 5,6-dihydroxyindole-2-carboxylic acid, 4-, 6- and 7-hydroxyindole, 6-amino-indole and 4-aminoindole.

Particular preference is attributed to derivatives of 5,6-dihydroxyindole corresponding to formula (Ib):

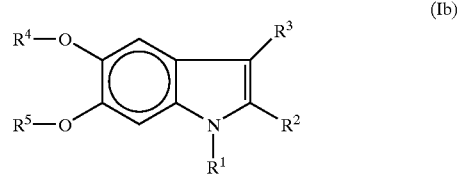

(Ib)

in which—independently of one another
R$^1$ is hydrogen, a C$_{1-4}$ alkyl group or a C$_{1-4}$ hydroxyalkyl group,
R$^2$ is hydrogen or a —COOH group which may even be present as a salt with a physiologically compatible anion,
R$^3$ is hydrogen or a C$_{1-4}$ alkyl group,
R$^4$ is hydrogen, a C$_{1-4}$ alkyl group or a group —CO—R$^6$ where R$^6$ is a C$_{1-4}$ alkyl group,
R$^5$ stands for one of the groups mentioned for R$^4$,
or a physiologically compatible salt of these compounds with an organic or inorganic acid.

According to the invention, preferred representatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole. The parent compound, 5,6-dihydroxyindole, is most particularly preferred.

The indoline and indole derivatives present in the formulations according to the invention may be used both as free bases and in the form of their physiologically compatible salts with inorganic or organic acids, for example hydrochlorides, sulfates and hydrobromides.

The indole or indoline derivatives are present in the formulations according to the invention in quantities of normally 0.05 to 10% by weight and preferably 0.2 to 5% by weight.

The present invention does of course also encompass formulations which contain more than one indoline or indole derivative or mixtures of indoline or indole derivatives.

In one particularly preferred embodiment, the formulations according to the invention contain no dyes or dye precursors other than the indoles or indolines mentioned.

In principle, however, other dye components or dye precursors could be used.

In the embodiments containing such additional compounds, the following substances are preferred:
Preferred primary intermediates:
p-phenylenediamine, p-toluylenediamine, p-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy-4,5,6-triaminopyrimidine, 4-hydroxy-2,5,6- triaminopyrimidine, 2,4-dihydroxy-5,6-diaminopyrimidine, 2-dimethylamino 4,5,6-triaminopyrimidine, 2-hydroxyethylaminomethyl-4-aminophenol, 4,4'-diaminodiphenylamine, 4-amino-3-fluorophenol, 2-aminomethyl-4-aminophenol, 2-hydroxymethyl-4-aminophenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 4-amino-2-(2-hydroxyethoxy)-phenol and 4,5-diaminopyrazole derivatives according to EP 0 740 741 and WO 94/108970 such as, for example, 4,5-diamino-1-(2'-hydroxyethyl)-pyrazole.

Particularly preferred primary intermediates:
p-phenylenediamine, p-toluylenediamine, p-aminophenol, 1-(2'-hydroxyethyl)-2,5-diaminobenzene, 4-amino-3-methylphenol, 4-amino-2-((diethylamino)-methyl)-phenol, 2,4,5,6-tetraaminopyrimidine, 2-hydroxy-4,5,6-triaminopyrimidine and 4-hydroxy-2,5,6-triaminopyrimidine.

Preferred secondary intermediates:
m-aminophenol and derivatives thereof such as, for example, 5-amino-2-methylphenol, 5-(3-hydroxypropylamino)-2-methylphenol, 3-amino-2-chloro-6-methylphenol, 2-hydroxy4-aminophenoxyethanol, 3-amino-6-methoxy-2-methylaminophenol, 2,6-dimethyl-3-aminophenol, 3-trifluoroacetylamino-2-chloro-6-methylphenol, 5-amino4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2,4-diaminophenoxy)-propane, 1-methoxy-2-amino-4-(2'-hydroxyethylamino)-benzene, 1,3-bis-(2,4-diaminophenyl)-propane, 2,6-bis-(2-hydroxyethylamino)-1-methylbenzene and 1-amino-3-bis-(2'-hydroxyethyl)-aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-3,4-diaminopyridine, 2,6-dihydroxy-4-methylpyridine, 2,6-diaminopyridine, 2,3-diamino-6-methoxy-pyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihdroxynaphthalene, 1,7-dihdroxy-naphthalene, 1,8-dihdroxynaphthalene, 2,7-dihdroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, methylenedioxybenzene derivatives such as, for example, 3,4-methylenedioxyphenol, 1-hydroxy-3,4-methylenedioxybenzene, 1-amino-3,4-methylenedioxybenzene and 1-(2'-hydroxyethyl)-amino-3,4-methylenedioxybenzene.

Particularly preferred secondary intermediates:
1-naphthol, 1,5-, 2,7- and 1,7-dihydroxynaphthalene, 3-aminophenol, 5-amino-2-methylphenol, 2-amino-3-hydroxypyridine, resorcinol, 4-chloro-resorcinol, 2-chloro-6-methyl-3-aminophenol, 2-methyl resorcinol, 5-methyl resorcinol, 2,5-dimethyl resorcinol, 2,6-dihydroxy-3,4-diaminopyridine.

Preferred substantive dyes are the compounds known under the International names or commercial names of HC Yellow 2, HC Yellow 4, HC Yellow 5, HC Yellow 6, Basic Yellow 57, Disperse Orange 3, HC Red 3, HC Red BN (4-Hydroxypropylamino-3-Nitrophenol), Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. Other preferred substantive dyes are naturally occurring dyes such as, for example, henna red, henna neutral, henna black, camomile blossom, sandalwood, black tea, black alder bark, sage, logwood, madder root, catechu, sedre and alkanet.

The oxidation dye precursors or the substantive dyes do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

With regard to the dyes suitable for use in the hair coloring and tinting formulations according to the invention, reference is also specifically made to Ch. Zviak's work The Science of Hair Care, Chapter 7 (pages 248–250; Substantive Dyes) and Chapter 8, pages 264–267; Oxidation Dye Precursors), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available in diskette form from the Bundesverband Deutscher Industrie- und Handelsunternehmen für Arzneimittel, Reformwaren und Körperpflegemittel e.V., Mannheim, Germany.

Both the oxidation dye precursors and the substantive dyes are present in the formulations according to the invention in quantities of preferably 0.01 to 20% by weight and preferably 0.5 to 5% by weight, based on the formulation as a whole.

Preferred formulations containing other dyes or dye precursors are those which do not contain an oxidation dye precursor of the primary intermediate type. In this embodiment of the invention, the corresponding formulations contain an oxidation dye precursor of the secondary intermediate type and, if desired, substantive dyes.

Other preferred formulations are those which do not contain an oxidation dye precursor of the secondary intermediate type. These formulations are also preferably free from oxidation dye precursors of the primary intermediate type, but may contain a substantive dye, preferably from the series of naturally occurring dyes.

To produce the colorants according to the invention, the compulsory and optional constituents mentioned above are incorporated in a suitable water-containing carrier. For coloring hair, such carriers are, for example, cremes, emulsions, gels or even surfactant-containing foaming solutions, for example shampoos, foam aerosols or other formulations suitable for application to the hair.

The hair colorants according to the invention are adjusted to a pH value of preferably 5 to 11 and, more preferably, 7 to 10.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly useful.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and—generally—ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—$(CH_2$—$CH_2O)_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—$O(CH_2$—$CH_2O)_x$—$SO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl amino-propionate, cocoacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group, $C_{12-22}$ fatty acid monoesters and diesters of products of the addition of 1 to 30 moles of ethylene oxide to glycerol, $C_{8-22}$ alkyl mono- and oligoglycosides and ethoxylated analogs thereof, products of the addition of 5 to 60 moles of ethylene oxide to castor oil and hydrogenated castor oil, products of the addition of ethylene oxide to sorbitan fatty acid esters, products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethi-cone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the corresponding products commercially available as Dehyquart®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/ vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose, maleic acid and lactic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol and diethylene glycol, antidandruff agents, such as Piroctone Olamine and Zinc Omadine, other substances for adjusting the pH value, for example $\alpha$- and $\beta$-hydroxycarboxylic acids, active substances, such as panthenol, pantothenic acid, allantoin, pyrrolidone carboxylic acids and salts thereof, plant extracts and vitamins, cholesterol, UV filters, consistency promoters, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

In one preferred embodiment, the color is developed with atmospheric oxygen as sole oxidizing agent.

In principle, however, a chemical oxidizing agent may also be used, particularly in cases where the formulations additionally contain oxidation dye precursors of the primary intermediate and secondary intermediate type. The same applies when human hair is to be not only colored, but also lightened. Particularly suitable oxidizing agents are hydrogen peroxide or addition products thereof with urea, melamine or sodium borate. Oxidation may also be carried out with enzymes. In this case, the enzymes may be used both to produce oxidizing per compounds and to enhance the effect of an oxidizing agent present in small quantities. One example of an enzymatic process is the procedure whereby the effect of small quantities (for example 1% and less, based on the formulation as a whole) of hydrogen peroxide is enhanced by peroxidases.

The preparation of the oxidizing agent is preferably mixed with the preparation of the oxidation dye precursors immediately before coloring of the hair. The ready-to-use hair coloring preparation formed should have a pH value in the range from 6 to 10. In a particularly preferred embodiment, the hair colorant is used in a mildly alkaline medium. The application temperatures may be in the range from 15 to 40° C. but are preferably at the temperature of the scalp. After a contact time of about 5 to 45 and preferably 15 to 30 minutes, the hair colorant is removed from the hair to be colored by rinsing. There is no need for the hair to be washed with a shampoo where a carrier of high surfactant content, for example a coloring shampoo, has been used.

In the particular case of hair which is difficult to color, the preparation containing the oxidation dye precursors may be applied to the hair without preliminary mixing with the oxidation component. The oxidation component is applied after a contact time of 20 to 30 minutes, optionally after rinsing. After another contact time of 10 to 20 minutes, the hair is rinsed and, if desired, shampooed. In a first variant of this embodiment where the preliminary application of the dye precursors is intended to improve penetration into the hair, the corresponding formulation is adjusted to a pH value of about 4 to 7. In a second variant, oxidation with air is initially carried out, the formulation applied preferably having a pH value of 7 to 10. In the subsequent accelerated post-oxidation phase, it can be of advantage to use acidified peroxydisulfate solutions as the oxidizing agent.

Whichever of the processes mentioned above is used to apply the colorant according to the invention, development of the color may be supported and enhanced by adding certain metal ions to the colorant. Examples of such metal ions are $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable. Basically, the metal ions may be used in the form of a physiologically compatible salt. Preferred salts are the acetates, sulfates, halides, lactates and tartrates. Zinc sulfate is a particularly preferred metal salt. Development of the hair color can be accelerated and the color tone can be influenced as required through the use of these metal salts.

The present invention also relates to the use of an amino acid or oligopeptide for intensifying and/or shading the colors in the coloring of keratin fibers with formulations containing an indoline derivative or an indole derivative as dye precursors.

The present invention also relates to a process for coloring human hair in which one of the formulations mentioned above is applied to the hair and the color is subsequently developed. In a preferred embodiment, the color is developed with atmospheric oxygen.

In one particular embodiment of this process, the final color is developed by repeated application of the formulation, followed after each application by oxidation with air. The formulation is preferably applied at intervals of about 1 day to about 2 weeks. Special tones can be selectively obtained in this way.

The following Examples are intended to illustrate the invention.

EXAMPLES

1. Coloring

Colorants with the compositions shown in Table 1 were first prepared [all quantities in grams [g] unless otherwise indicated].

Coloring was carried out on hair tresses about 5 cm long and weighing about 0.5 g. 1 g of the formulation to be tested was applied to the hair. After 20 minutes (oxidation with air), the formulation was rinsed out with water and the hair was washed with a commercially available shampoo. The colors listed in Table 2 correspond to the conditions after storage of the tresses for one day at room temperature under standard air humidity conditions (ca. 50% relative humidity).

TABLE 1

| Component | formulations | | | | |
|---|---|---|---|---|---|
| | E1 | E2 | C1 | C2 | C3 |
| Stenol ® 1618 O[1] | 6.7 | 6.7 | 6.7 | 6.7 | 6.7 |
| Lorol ® techn[2] | 2.0 | 2.0 | 2.0 | 2.0 | 2.0 |
| Eumulgin ® B 2[3] | 2.0 | 2.0 | 2.0 | 2.0 | 2.0 |
| Ascorbic acid | 0.2 | 0.2 | 0.2 | 0.2 | 0.2 |
| Ammonium sulfate | — | — | 1.0 | — | — |
| 5,6-Dihydroxyindoline hydrobromide | 1.0 | — | 1.0 | 1.0 | — |
| 5,6-Diacetoxyindole | — | 1.0 | — | — | 1.0 |
| Potassium hydroxide to pH 9.5 | — | — | X | X | X |
| Arginine (to pH 9.5) | 3.0 | 3.0 | — | — | — |
| Water | to 100 | | | | |

$C_{16-18}$ fatty alcohol (HENKEL)
$C_{12-18}$ fatty alcohol (HENKEL)
Cetylstearyl alcohol containing ca. 20 moles EO (CTFA name: Ceteareth-20) (HENKEL)

TABLE 2 colors [depth of color/shade]

| Formulation | Blond human hair (Kerling natural white) | Grey human hair (Klugmann natural medium grey #6623) |
|---|---|---|
| E1 | Medium blond dark blond/ grey with slight blue tinge | Medium brown/ with slight blue tinge (flat medium brown) |
| E2 | Medium blond/ grey with slight blue tinge | Light brown/ neutral, no blue tinge visible |
| C1 | Medium blond/ natural color with slight red tinge | Light brown/ natural color with slight red tinge |
| C2 | Light blond-medium blond/ bluish | Dark blond/ with slight blue tinge |
| C3 | Light blond/ slight blue tinge | Dark blond/ neutral, no blue tinge visible |

What is claimed:

1. A composition for restoring gray keratin fibers to a natural color comprising:

a) from 0.05 percent by weight to 10 percent by weight of a dye precursor comprising at least one indoline or indole, wherein the indoline or indole serves as a precursor to melanin; and b) from 0.1 percent by weight to 10 percent by weight of an alpha-aminocarboxylic acid selected from the group consisting of arginine, ornithine, lysine, histidine, and mixtures thereof, wherein the alpha-aminocarboxylic acid has a pH of 9 or greater in water at a concentration of 2.5 percent by weight, wherein the composition restores gray keratin fibers to their natural color, and wherein said weight percents are based on the total weight of the composition.

2. The composition of claim 1 wherein the indoline or the indole contains at least one hydroxy or amino group on the six membered ring.

3. The composition of claim 1 wherein the dye precursor comprises (i) an indoline compound

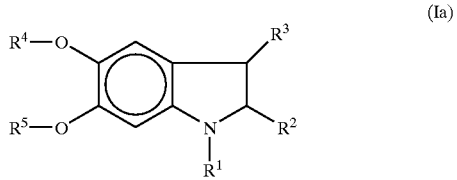

(Ia)

corresponding to formula (Ia):
wherein, independently of one another, $R^1$ is hydrogen, a $C_{1-4}$ alkyl group or a $C_{1-4}$ hydroxyalkyl group, $R^2$ is hydrogen or a —COOH group or salt thereof, $R^3$ is hydrogen or a $C_{1-4}$ alkyl group, $R^4$ is hydrogen, a $C_{1-4}$ alkyl group or a —CO—$R^6$ group where $R^6$ is a $C_{1-4}$ alkyl group, and $R^5$ stands for one of the groups mentioned for $R^4$; or
(ii) a physiologically compatible salt of a compound of formula Ia with an organic or inorganic acid.

4. The composition of claim 1 wherein the dye precursor comprises (i) an indole compound corresponding to formula (Ib):

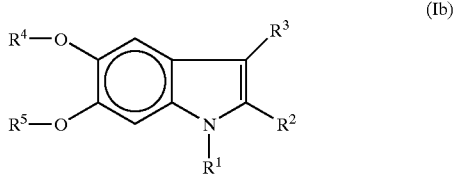

(Ib)

wherein, independently of one another, $R^1$ is hydrogen, a $C_{1-4}$ alkyl group or a $C_{1-4}$ hydroxyalkyl group, $R^2$ is hydrogen or a —COOH group or salt thereof, $R^3$ is hydrogen or a $C_{1-4}$ alkyl group, $R^4$ is hydrogen, a $C_{1-4}$ alkyl group or a —CO—$R^6$ group where $R^6$ is a $C_{1-4}$ alkyl group, and $R^5$ stands for one of the groups mentioned for $R^4$; or
(ii) a physiologically compatible salt of a compound of formula (Ib) with an organic or inorganic acid.

5. The composition of claim 1 wherein the indoline or the indole is 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 4-hydroxyindole, 6-hydroxyindole, 7-hydroxyindole, 6-aminoindole, or 4-aminoindole, or a physiologically compatible salt thereof.

6. The composition of claim 1 wherein the dye precursor further comprises at least one primary intermediate selected from the group consisting of p-phenylenediamine, p-toluylenediamine, p-aminophenol, 1-(2'-hydroxyethyl)-2,5-diaminobenzene, 4-amino-3-methylphenol, 4-amino-2-((diethylamino)-methyl)-phenol, 2,4,5,6-tetraaminopyrimidine, 2-hydroxy-4,5,6-triamiopyrimidine, 4-hydroxy-2,5,6-triaminopyrimidine and combinations thereof.

7. The composition of claim 1 wherein the dye precursor further comprises at least one secondary intermediate selected from the group consisting of 1-naphthol, pyrogallol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol, 2,6-dihydroxy-3,4-diaminopyridine, a physiologically compatible salt thereof, and combinations thereof.

8. The composition of claim 1 further comprising at least one substantive dye selected from the group consisting of HC Yellow 2, HC Yellow 4, HC Yellow 5, HC Yellow 6, Basic Yellow 57, Disperse Orange 3, HC Red 3, 4-hydroxypropylamino-3-nitrophenol, Basic Red 76, HC Blue 2, HC Blue 12, Disperse Blue 3, Basic Blue 99, HC Violet 1, Disperse Violet 1, Disperse Violet 4, Disperse Black 9, Basic Brown 16, Basic Brown 17, 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid, 2-chloro-6-ethylamino-1-hydroxy-4-nitrobenzene, and combinations thereof.

9. The composition of claim 1 further comprising at least one naturally occurring substantive dye selected from the group consisting of henna red, henna neutral, henna black, camomile blossom, sandalwood, black tea, black alder bark, sage, logwood, madder root, catechu, sedre, alkanet and combinations thereof.

10. The composition of claim 1 wherein the indoline or indole is present in an amount of from 0.2 percent by weight to 5 percent by weight based on the total weight of the composition.

11. The composition of claim 1 wherein the restored color is dark brown to black and the composition further comprises at least one secondary intermediate selected from the group consisting of 1-naphthol pyrogallol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol, 2,6-dihydroxy-3,4-diaminopyridine, a physiologically compatible salt thereof, and combinations thereof.

12. The composition of claim 1 wherein the composition contains no other dyes or dye precursors, except for the indoline or indole.

13. A method of restoring gray keratin fibers to their natural color comprising
(a) forming a composition comprising
(i) a dye precursor comprising at least one indoline, indole, or derivative thereof, wherein the indoline, indole or derivative thereof serves as a precursor to melanin; and
(ii) an alpha-aminocarboxylic acid selected from the group consisting of arginine, ornithine, lysine, histidine, and mixtures thereof, wherein the alpha-aminocarboxylic acid has a pH of 9 or greater in water at a concentration of 2.5 percent by weight; and (b) applying the composition to gray keratin fibers to restore the gray keratin fibers to their natural color.

14. The method of claim 13 wherein the composition has a pH of 5 to 11.

15. The method of claim 14 further comprising oxidizing the composition using atmospheric oxygen as the sole oxidizing agent.

16. The method of claim 15 further comprising reapplying the composition to the keratin fibers one or more times and oxidizing the composition with air after each of the applications to effect a desired final color.

17. A composition for coloring keratin fibers comprising
(a) a dye precursor comprising at least one indoline or indole; and
(b) an alpha-aminocarboxylic acid selected from the group consisting of arginine, ornithine, lysine, histidine, and mixtures thereof having a pH of 9 or greater in water at a concentration of 2.5 percent by weight; wherein the composition contains no other dye precursor or dye, except for the indoline or indole.

* * * * *